United States Patent
Li et al.

(10) Patent No.: US 11,963,519 B2
(45) Date of Patent: Apr. 23, 2024

(54) KIT AND METHOD FOR CONSTRUCTING LONG-ACTING DEPRESSION ANIMAL MODEL

(71) Applicant: Northwest Institute of Plateau Biology, CAS, Xining (CN)

(72) Inventors: Cen Li, Xining (CN); Hongxia Yang, Xining (CN); Jing Zhao, Xining (CN); Lixin Wei, Xining (CN); Yuzhi Du, Xining (CN); Yuancan Xiao, Xining (CN); Hongtao Bi, Xining (CN); Zhanjuan Chen, Xining (CN); Yajun Qiao, Xining (CN); Jianv Wang, Xining (CN)

(73) Assignee: Northwest Institute of Plateau Biology, CAS, Xining (CN)

( * ) Notice: Subject to any disclaimer, the term of this patent is extended or adjusted under 35 U.S.C. 154(b) by 0 days.

(21) Appl. No.: 17/895,405

(22) Filed: Aug. 25, 2022

(65) Prior Publication Data
US 2023/0329200 A1    Oct. 19, 2023

(30) Foreign Application Priority Data

Apr. 13, 2022  (CN) .......................... 202210384349.4

(51) Int. Cl.
*A01K 67/02*    (2006.01)
*C07K 14/235*   (2006.01)
*C07K 14/35*    (2006.01)

(52) U.S. Cl.
CPC ............ *A01K 67/02* (2013.01); *C07K 14/235* (2013.01); *C07K 14/35* (2013.01); *A01K 2227/105* (2013.01); *A01K 2267/0356* (2013.01)

(58) Field of Classification Search
CPC .................. C07K 14/235; C07K 14/35; A01K 2267/0356
See application file for complete search history.

(56) References Cited

PUBLICATIONS

Moreau (2008, Brain, Behavior, and immunity, 22:1087-1095).*
Hofstetter (2002, Journal of Immunology, 169:117-125).*
Peruga (2011, Behavioural Brain Research, 220:20-29).*

* cited by examiner

*Primary Examiner* — Valarie E Bertoglio
(74) *Attorney, Agent, or Firm* — Mark C. Johnson; Johnson Dalal (57) ABSTRACT

The present disclosure provides a kit and method for constructing a long-acting depression animal model. The present disclosure adopts Bacille Calmette-Guerin (BCG) (or *Mycobacterium bovis* (*M bovis*)) and low-dose pertussis toxin (PTX) for combined induction, which greatly reduces modeling cost. A mouse model constructed by the method of the present disclosure can clearly distinguish a time interval of pathological behaviors from a time interval of depression-like behaviors and has prominent face validity and predictive validity. The method of the present disclosure is simple and convenient and does not require a large number of tedious daily operations as the depression model construction by chronic unpredictable stress, chronic restraint stress, social defeat, mother-child separation, or the like. The mouse model of the present disclosure can provide a valuable long-term intervention window for research on antidepressant therapy.

5 Claims, 5 Drawing Sheets

KIT AND METHOD FOR CONSTRUCTING LONG-ACTING DEPRESSION ANIMAL MODEL

CROSS-REFERENCE TO RELATED APPLICATION

This patent application claims the benefit and priority of Chinese Patent Application No. 202210384349.4, entitled Kit And Method For Constructing Long-Acting Depression Animal Model filed on Apr. 13, 2022, the disclosure of which is incorporated by reference herein in its entirety as part of the present application.

TECHNICAL FIELD

The present disclosure belongs to the technical field of animal models, and in particular, relates to a kit and method for constructing a long-acting depression animal model.

BACKGROUND ART

Depression is a global mental disorder that seriously endangers people's health, which has the characteristics of high prevalence rate, high recurrence rate, high disease burden, high self-injury rate, and high suicide rate and is mainly manifested as symptoms such as persistent extremely-depressed mood, declined volitional activity, impaired cognitive function, and inhibition of thinking (Gao Guiyuan, Huang Jie, Liu Dan, Zhang Fang, Zhang Chaoqun, Zhang Guoli, Chen Lihua, Shao Yingxin. Pathogenesis of Depression and Research Progress of Antidepressant Drugs. China Medical Herald, 2021, 18 (01): 52-55.). According to data from the World Health Organization (WHO) in 2017, about 322 million people worldwide suffer from depression, with a prevalence rate of about 4.4% (World Health Organization. Depression and other common mental disorders: global health estimates (Report). 2017, 1-24). The Depression animal model is a cornerstone of research on antidepressant drugs and depression therapies. Common animals for modeling are rodents, and there are mainly five model construction methods: social environmental stress modeling, drug-based modeling, surgical process modeling, genetic modeling, and inflammation-based depression model construction.

Maïte Moreau and other researchers at University of Illinois at Urbana-Champaign first reported in 2008 that the injection of Bacille Calmette-Guerin (BCG, including *Mycobacterium bovis* (*M bovis*)) in mice can induce long-term depression-like symptoms based on immune inflammation (Moreau M, André C, O'Connor J C, et al. InocpLation of *Bacillus* Calmette-Guerin to mice induces an acute episode of sickness behavior followed by chronic depression-like behavior. Brain Behav Immun. 2008; 22 (7): 1087-1095. doi:10.1016/j.bbi.2008.04.001). This model is one of the immunostimulatory depression models and has a prominent anticipation effect. However, a dose of BCG with high bacterial activity required for inducing this model is generally in the order of $10^7$ to $10^9$ CFU/mouse (Maite Moreau, Jacques Lestage, Daniele Verrier, Cecile Mormede, Keith W. Kelley, Robert Dantzer, Nathalie Castanon, Bacille Calmette-Guérin InocpLation Induces Chronic Activation of Peripheral and Brain Indoleamine 2,3-Dioxygenase in Mice, The Journal of Infectious Diseases, Volume 192, Issue 3, 1 Amust 2005), and each mouse requires a high dose of BCG, which results in a high cost of BCG or *M. bovis* modeling. Therefore, there is an urgent need to develop a method that can reduce the dose of BCG or *M bovis* while inducing significant long-term depression-like behaviors.

Compared with social environmental stress, drug, surgical, and genetic modeling for constructing depression models, the method for constructing a depression model through immune activation is relatively simple, exhibits prominent face validity, construct validity, and predictive validity, and has promising application prospects in antidepressant drug screening and depression pathogenesis. However, such a model generally has the following three shortcomings: 1. depression-like behaviors and pathological behaviors sometimes are not distinguished easily; 2. duration time of depression-like behaviors is short; 3. sometimes the model is not very stable. BCG-induced depression models overcome these three shortcomings to a large extent and exhibit a longer duration time of depression-like behaviors, such that the interval of pathological behaviors is easily distinguished from the interval of depression-like behaviors. However, there is also a very important problem that needs to be solved, that is, each mouse requires a very high dose of BCG, which greatly increases the cost of constructing a pharmacological experimental animal model.

SUMMARY

In view of this, the present disclosure is intended to provide a kit and method for constructing a long-acting depression animal model, breaking through the technical bottleneck in which only at a high BCG dose can the long-acting depression mouse model be successfully induced and reducing the cost for modeling.

To achieve the above objective, the present disclosure provides the following technical solutions.

The present disclosure provides a method for constructing a long-acting depression animal model, and the method includes a step of using both BCG and pertussis toxin (PTX) for combined induction.

Preferably, the combined induction includes: injecting a working solution of BCG into a model animal on day 0; and injecting a working solution of PTX into the model animal on day 0 to day 1 and day 2 to day 3.

Preferably, the working solution of BCG is prepared through the following step: diluting BCG with 1× phosphate-buffered saline (PBS) or normal saline (NS) until a colony forming unit (CFU) concentration of *M bovis* is $1 \times 10^6$ to $6 \times 10^7$ CFU/mL to obtain the working solution.

Preferably, the working solution of PTX is prepared through the following steps: dissolving PTX in ultrapure water (UPW) to prepare a 200 µg/mL stock solution; and diluting the stock solution to 0.5 µg/mL to 4 µg/mL with 1× PBS or NS to obtain the working solution.

Preferably, the model animal is a mouse.

The present disclosure also provides a method for constructing a long-acting depression mouse model, including the following steps: intraperitoneally injecting 50 µL to 400 µL of working solution of BCG into a mouse on day 0, and intraperitoneally injecting 50 µL to 400 µL of working solution of PTX into the mouse on day 0 to 1 and days 2 to 3;

where the working solution of BCG has an *M bovis* CFU concentration of $1 \times 10^6$ to $6 \times 10^7$ CFU/mL; and the working solution of PTX has a concentration of 0.5 µg/mL to 4 µg/mL.

Preferably, an *M. bovis* CFU dose of BCG is $1 \times 10^5$ to $5 \times 10^6$ CFU/mouse; and PTX may be intraperitoneally injected at a dose of 50 to 800 ng/mouse/injection.

The present disclosure also provides a kit for constructing a long-acting depression animal model, including BCG and PTX that are individually packed.

Preferably, the kit further includes UPW, PBS, and NS for dissolution and/or dilution.

The present disclosure also provides the use of the animal model obtained by the method described above or the mouse model obtained by the method described above in screening or identifying a drug capable of preventing, alleviating, or treating depression and/or a vaccine capable of preventing depression.

Beneficial effects: The present disclosure provides a method for constructing a long-acting depression animal model, where BCG and low-dose PTX are used for combined induction, which greatly reduces the modeling cost of the model. A mouse model constructed by the method of the present disclosure can clearly distinguish a time interval of pathological behaviors from a time interval of depression-like behaviors and has prominent face validity and predictive validity. The method of the present disclosure is simple, convenient, and does not require a large number of tedious daily operations as the depression model such as chronic unpredictable stress, chronic restraint stress, social defeat, mother-child separation, or the like. The mouse model of the present disclosure can provide a valuable long-term intervention window for research on antidepressant therapy.

DETAILED DESCRIPTION OF THE EMBODIMENTS

The present disclosure provides a method for constructing a long-acting depression animal model, including the following step: using BCG and PTX for combined induction.

In use, BCG (with $M$ $bovis$ being the component) of the present disclosure is preferably diluted to a concentration of a working solution; and the working solution is preferably prepared through the following step: diluting BCG with 1× PBS or NS until a CFU concentration of $M$ $bovis$ is $1\times10^6$ to $6\times10^7$ CFU/mL to obtain the working solution. In the present disclosure, there are no special limitations on the source of BCG or *M bovis*, and conventional commercially-available BCG or *M bovis* in the art can be used, for example, those purchased from Chengdu Institute of Biological Products Co., Ltd., Shanghai Institute of Biological Products Co., Ltd., or French Sanofi Company.

In use, PTX of the present disclosure is preferably diluted to a concentration of a working solution; and the working solution is preferably prepared through the following steps: dissolving PTX in UPW to prepare a 200 μg/mL stock solution; and diluting the stock solution to 0.5 μg/mL to 4 μg/mL with 1× PBS or NS to obtain the working solution. In the present disclosure, there are no special limitations on a source of PTX, and conventional commercially-available products in the art may be used, for example, those purchased from List Biological Labs (50 μg/bottle, #180 or #181). In the present disclosure, the stock solution is preferably prepared as follows: 1 bottle of PTX is taken, 250 μL of UPW is pipetted and added to the bottle, and then the bottle is shaken to obtain a clear solution as PTX stock solution with a concentration of 200 μg/mL and stored at 4° C. for a long time. In the present disclosure, the working solution of PTX is preferably prepared just before use; and the working solution of PTX can be prepared by diluting PTX with 1× PBS or NS to the target concentration.

In the present disclosure, the combined induction preferably includes: injecting a working solution of BCG into a model animal on day 0, and injecting a working solution of PTX into the model animal on day 0 to 1 and day 2 to 3. In the present disclosure, the model animal is preferably a mouse.

The present disclosure also provides a method for constructing a long-acting depression mouse model, including the following steps: intraperitoneally injecting 50 μL to 400 μL of a working solution of BCG into a mouse on day 0, and intraperitoneally injecting 50 μL to 400 μL of a working solution of PTX into the mouse on days 0 to 1 and days 2 to 3;

where the working solution of BCG has an *M bovis* CFU concentration of $1\times10^6$ to $6\times10^7$ CFU/mL; and the working solution of PTX has a concentration of 0.5 μg/mL to 4 μg/mL.

The preparation methods of the working solution of BCG and the working solution of PTX of the present disclosure may be the same as described above and will not be repeated herein. In an embodiment of the present disclosure, the selected mice are preferably healthy adult CD-1 mice, which cannot be deemed as the entire protection scope of the present disclosure. In the present disclosure, when the mouse is used for modeling, a CFU dose of BCG is preferably $1\times10^5$ to $5\times10^6$ CFU/mouse; and PTX may be intraperitoneally injected at a dose of 50 to 800 ng/mouse/injection.

In the present disclosure, a significant long-acting depression mouse model can be induced with a combination of PTX and BCG at a low BCG dose, and an *M bovis* CFU dose used for BCG can be as low as $1\times10^5$ CFU/mouse. In the depression model of the present disclosure, the time interval of pathological behaviors and the time interval of depression-like behaviors are clearly distinguished: the time interval of the mixed state of pathological behaviors plus depression-like behaviors takes place from about day 1 to day 7 after modeling, the mice basically enters a time interval dominated by depression-like behaviors on about day 7, and the depression-like behaviors can last at least until day 28 after modeling. The mice in the depression model of the present disclosure exhibit significantly-reduced exploratory behaviors, increased behavioral despair, increased avoidance behaviors, and the like.

The present disclosure also provides a kit for constructing a long-acting depression animal model, including BCG and PTX that are individually packed.

In the present disclosure, there are no special limitations on the contents of BCG and PTX in the kit, and a concentration of a working solution obtained by dilution can be adopted. The kit of the present disclosure may preferably further include UPW, PBS, and NS for dissolution and/or dilution.

The present disclosure also provides the use of the animal model obtained by the method described above or the mouse model obtained by the method described above in screening or identifying a drug capable of preventing, alleviating, or treating depression and/or a vaccine capable of preventing depression.

The animal model or mouse model obtained by the construction method of the present disclosure can retain other advantages of BCG model, is stable, and can provide a valuable long-term intervention window for research on antidepressant therapy.

The method for constructing a long-acting depression animal model provided by the present disclosure is described in detail below by referring to the examples, but these examples may not be understood as limiting the protection scope of the present disclosure.

Example 1

(1) Preparation of PTX stock solution: A bottle of PTX (List Biological Labs, 50 μg/bottle, LOT: #181) was taken, 250 μL of UPW was pipetted and added to the bottle, and then the bottle was shaken to obtain a clear solution as the PTX stock solution with a concentration of 200 μg/mL and stored at 4° C. for a long time.

(2) Preparation of PTX working solution: the PTX stock solution with a concentration of 200 μg/mL was diluted with 1×PBS to obtain the PTX working solution with a concentration of 1 μg/mL, which was prepared just before use.

(3) Preparation of BCG suspension: BCG (Chengdu Institute of Biological Products Co., Ltd.) was prepared with NS into a suspension with a CFU concentration of $2\times10^7$ CFU/mL.

(4) Preparation of solution of positive control drug imipramine (IMI): an IMI solution with a concentration of 1.5 mg/mL was prepared with NS.

(5) Subject animals and modeling treatment: 8-week-old SPF-grade healthy male CD-1 mice were selected and divided into a blank (Control) group, a BCG+PTX group, and a BCG+PTX+IMI group, with 15 mice in each group.

The mice in the blank (Control) group were intraperitoneally injected (i.p.) with sterile NS at a dose of 200 μL/mouse.

The mice in the BCG+PTX group were intraperitoneally injected with 200 μL of a BCG suspension at a dose of $4\times10^6$ CFU/mouse on day 0, and then intraperitoneally injected with 200 μL of a PTX working solution at a dose of 200 ng/mouse on day 1 and day 3.

The mice in the BCG+PTX+IMI group were intraperitoneally injected with 200 μL of a BCG suspension at a dose of $4\times10^6$ CFU/mouse on day 0, and intraperitoneally injected with 200 μL of PTX working solution at a dose of 200 ng/mouse on day 1 and day 3. The mice in the BCG+PTX+IMI group were intragastrically administered with IMI every day from day 0 at a dose of 15 mg/kg for 28 consecutive days.

Note: IMI is a clinical first-line tricyclic antidepressant drug and is often used as a positive control drug in antidepressant research.

(6) Raising conditions: 5 tested CD-1 mice were raised in each cage, and the raising of the mice in a single cage individually was avoided. The mice were raised in a barriered environment, and a water bottle filled with pure water and a sterile feed were placed in each cage. The mice were raised at a temperature of 22° C. and a humidity of 50%, with a 12 h light/12 h dark cycle.

(7) Monitoring pathological behaviors by monitoring body weight changes

The body weight was measured once every day from day 4 before modeling to day 7 after modeling, and then measured once every 1 to 3 days from day 8 after modeling until the end of the experiment. The body weight changes were monitored to monitor the response of mice to pathological behaviors.

Figure 1:
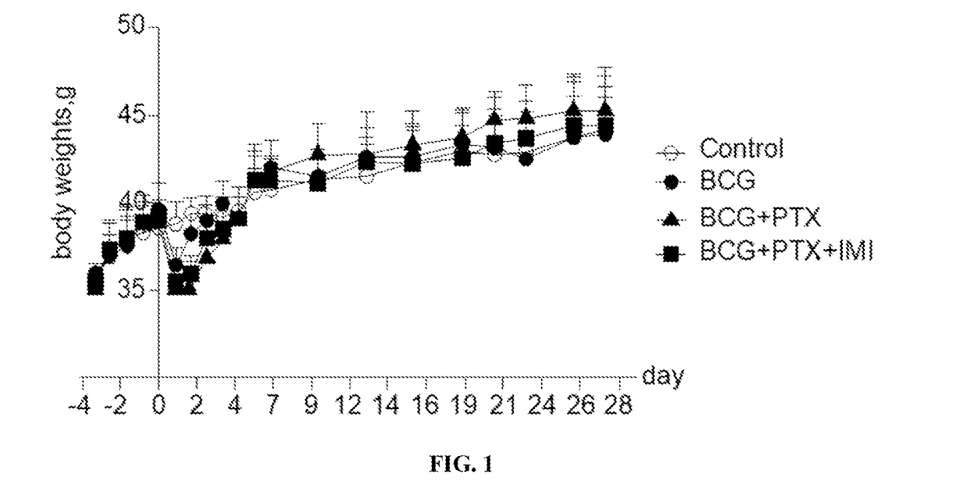
FIG. 1 shows the body weight changes of mice in each treatment group of Example 1 (n=15, Mean±SD)

Results are shown in FIG. 1. In the modeling group in which a combination of BCG and PTX was used for modeling, the body weight of CD-1 mice dropped sharply with a decrease larger than that in the modeling group in which BCG alone was used, and then the body weight gradually recovered and was recovered to the same level as the CD-1 mice in the control group on day 5, indicating that the mice had recovered from the pathological state at this point.

(8) Assessment of depression-like behaviors
1) Open-Field Test

The exploratory behaviors, depression-anxiety states, and spontaneous motor behaviors of mice were assessed by an open-field test before modeling and on day 6 and day 27 after modeling. Specific method: according to the description reported by Porsolt et al. (reference PMID: 11378179), mice were transferred to an open-field test room 60 min before the experiment, and during the experiment, the mice were taken out from cages and placed in the center of an open-field test device (50×50×415 mm), and the sunshade curtain of the experimental station was quickly drawn. The mouse number, date, and state were recorded in the operating software, a recording system was opened, a nine-square grid mode was selected, and the proportion of the central zone was set to 0.5. A camera above the open-field device and a monitor connected thereto were used to record the movements of the mice within 5 min to 10 min, including movement time, rest time, movement distance, residence time in the central zone, number of times for crossing the central zone, standing behaviors, and the like. After the experiment was completed, the mice were put back into respective cages, and the experiment device was thoroughly wiped with 70% ethanol and wipe-dried with paper towels.

2) Tail Suspension Test

The behavioral despair states of the mice were assessed by the tail suspension test on day 28 after modeling. Specific method: the method reported by Stem et al. (reference PMID: 3923523) was slightly modified, and according to the modified method, the mice were transferred to a quiet test room 60 min before the test to reduce the nervousness of animals. During the test, the mouse tail was fixed with adhesive tape (2 cm to 3 cm away from the tip of the mouse tail) and hung on a test frame, and the test lasted for 6 min. The whole process of the test was recorded by a digital camera, and then the timer or tail suspension test analysis software (SuperTst, Shanghai Xinruan Information Technology Co., Ltd.) was used to record the total time during which the mice remained motionless within the last 4 min in a double-blind manner. Motionlessness time was defined as a time during which a mouse was completely motionless after being suspended.

Figure 2:
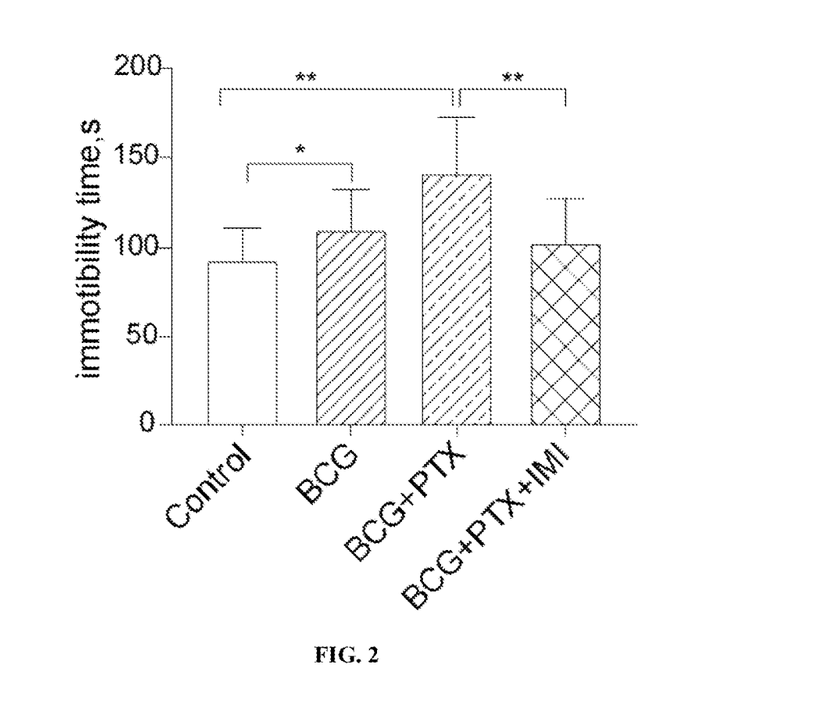
FIG. 2 shows the results for the tail-suspension test (TST) in mice in each treatment group of Example 1 on day 28 (n=15, Mean±SD)

Results are shown in FIG. 2. On day 28 of modeling, the motionlessness time of the mice in the BCG+PTX modeling group was significantly longer than that of the mice in the blank group (p<0.01) and superior to that of the mice in the BCG modeling group (p<0.05) during the TST; and the positive control drug IMI could improve the motionlessness time of the mice in the BCG+PTX combined modeling group.

(9) Evaluation results of the constructed depression mouse model 2) The constructed depression mouse model exhibited prominent face validity: the mice in the BCG+PTX group were recovered from the pathological state to a normal state on day 5, and then began to exhibit depression-like behaviors that were not disturbed by the pathological behaviors, which lasted at least until day 28, for example, the behavioral despair state in the TST ($p<0.01$) and the number of times of zone crossing ($p<0.01$), the exploratory behaviors ($p<0.001$), and the total movement distance ($p<0.01$) in the open-field test were increased.

Figure 3:
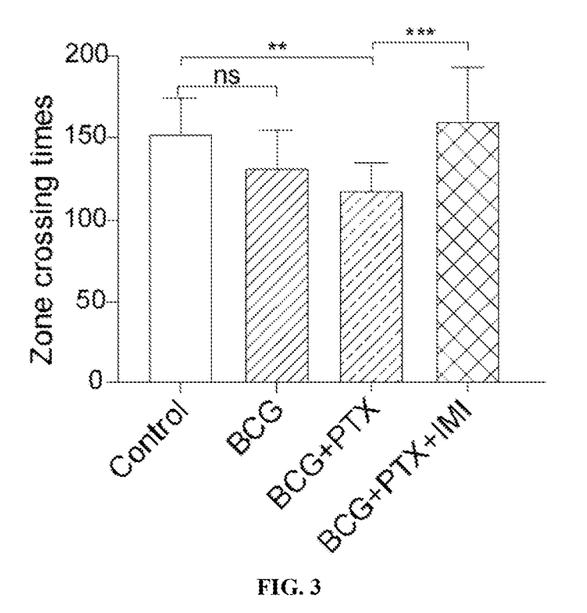
FIG. 3 shows the number of times of zone crossing of mice in each treatment group of Example 1 on day 27 in an open-field test (n=15, Mean±SD)
Figure 4:
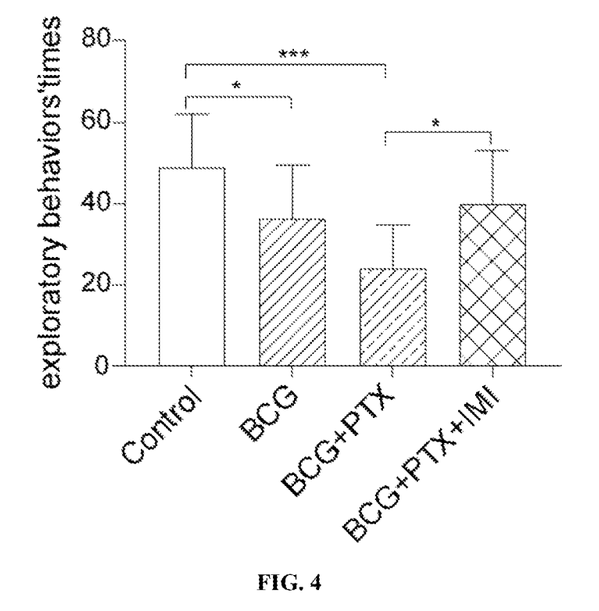
FIG. 4 shows the number of times of exploratory behaviors of mice in each treatment group of Example 1 on day 27 in an open-field test (n=15, Mean±SD)
Figure 5:
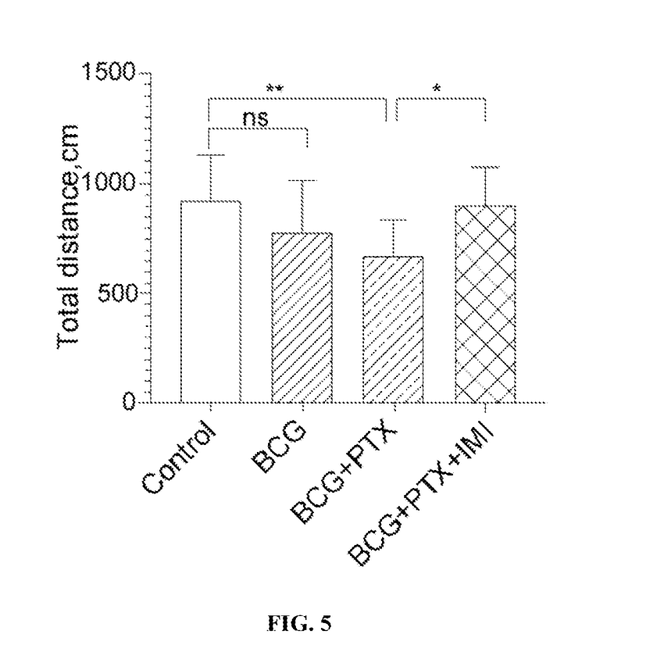
FIG. 5 shows the total movement distance of mice in each treatment group of Example 1 on day 27 in an open-field test (n=15, Mean±SD)

Results are shown in FIG. 3, FIG. 4, and FIG. 5. It can be seen in FIG. 3 that the combined induction with BCG and PTX could significantly reduce the number of times of zone crossing ($p<0.01$), the number of times of exploratory behaviors ($p<0.001$), and total movement distance ($p<0.01$) of CD-1 mice, which were superior to that of the modeling with BCG alone.

2) The constructed depression mouse model exhibited prominent predictive validity: the clinical classic tricyclic antidepressant drug IMI could preventively and significantly alleviate depression-like behaviors in depression model mice. For example, the behavioral despair state in the TST ($p<0.01$, FIG. 2) was improved, and the number of times of zone crossing ($p<0.001$, FIG. 3), the exploratory behaviors ($p<0.05$, FIG. 4), and the total movement distance ($p<0.05$, FIG. 5) in the open-field test were increased.

Example 2

(6) Preparation of PTX stock solution: a bottle of PTX (List Biological Labs, 50 μg/bottle, LOT: #180) was taken, 200 μL of UPW was pipetted and added to the bottle, and then the bottle was shaken to obtain a clear solution as the PTX stock solution with a concentration of 250 μg/mL and stored at 4° C.

(7) Preparation of PTX working solution: the PTX stock solution with a concentration of 250 μg/mL was diluted with NS to obtain the PTX working solution with a concentration of 2 μg/mL, which was prepared just before use.

(8) Preparation of BCG suspension: BCG (Chengdu Institute of Biological Products Co., Ltd.) was prepared with 1×PBS into a suspension with a CFU concentration of $2\times10^6$ CFU/mL.

(9) Preparation of solution of positive control drug (fluoxetine hydrochloride): an IMI solution with a concentration of 1.5 mg/mL was prepared with NS.

(10) Subject animals and modeling treatment: 10-week-old SPF-grade healthy male CD-1 mice were selected and divided into a blank (Control) group, a BCG+PTX group, and a BCG+PTX+IMI group, with 12 mice in each group.

The mice in the blank (Control) group were intraperitoneally injected (i.p.) with sterile NS at a dose of 400 μL/mouse.

The mice in the BCG+PTX group were intraperitoneally injected with 400 μL of a $2\times10^6$ CFU/mL BCG suspension at a dose of $8\times10^5$ CFU/mouse on day 0, and then intraperitoneally injected with 200 μL of a 2 μg/mL PTX solution at a dose of 400 ng/mouse on day 1 and day 3.

The mice in the BCG+PTX+IMI group were intraperitoneally injected with 400 μL of a $2\times10^6$ CFU/mL BCG suspension at a dose of $8\times10^5$ CFU/mouse on day 0, and intraperitoneally injected with 200 μL of a 200 μg/mL PTX solution at a dose of 400 ng/mouse on day 1 and day 3, and the mice in the BCG+PTX+IMI group were intragastrically administered with the positive control drug IMI every day from day 0 at a dose of 15 mg/kg for 28 consecutive days.

Note: IMI is a clinical first-line tricyclic antidepressant drug and is often used as a positive control drug in antidepressant research.

(6) Raising conditions: 4 tested CD-1 mice were raised in each cage, and raising the mice in a single cage individually was avoided. The mice were raised in a barriered environment, and a water bottle filled with pure water and a sterile feed were placed in each cage. The mice were raised at a temperature of 23° C. and a humidity of 55%, with a 12 h light/12 h dark cycle.

(7) Monitoring of body weight changes

The body weight was measured once every day from day 4 before modeling to day 7 after modeling, and then measured once every 1 to 3 days from day 8 after modeling until the end of the experiment. The body weight changes were monitored to monitor the response of mice to pathological behaviors.

(8) Assessment of depression-like behaviors
1) Sucrose preference test

The sucrose preference test was conducted on day 27 after modeling. The sucrose preference test was conducted mainly to evaluate one of the core symptoms of depressed mice (anhedonia) according to the method reported in the literature (reference PMID: 19632285). The sucrose adaptive training was conducted during the first 72 hours. Two water bottles were placed in each cage, with one bottle filled with 2% sucrose aqueous solution and the other bottle filled with tap water; and the positions of the two water bottles were exchanged every 12 h. After became adapted to sucrose, the mice were deprived of food and drinking water for 23 h. The sucrose preference test was conducted at 7:00 p.m. on day 28, and mice in each cage were given both a bottle of 2% sucrose and a bottle of tap water, the mice were allowed to drink water freely Two hours later, the consumption of sucrose and the consumption of tap water were determined, the sucrose preference rate was calculated according to the following formula:

sucrose preference rate=sucrose consumption/(sucrose consumption+tap water consumption)×100%.

Figure 6:
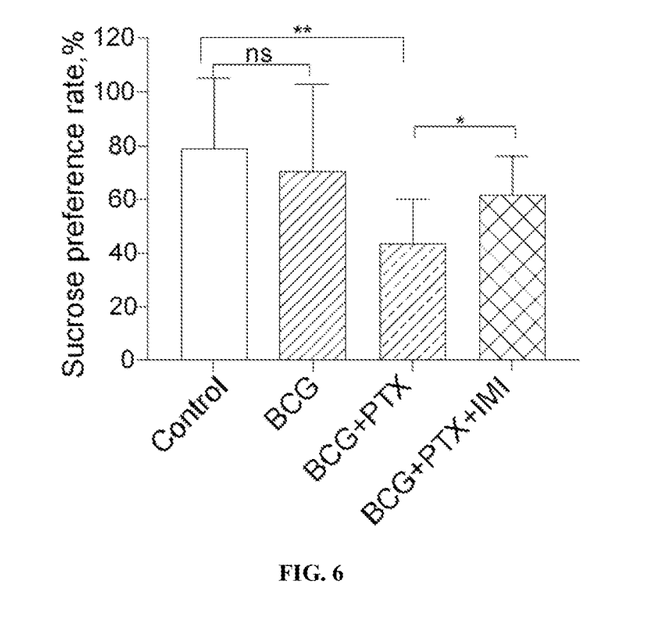
FIG. 6 shows the sucrose preference rate of mice in each treatment group of Example 2 on day 27 (n=12, Mean±SD)

The results are shown in FIG. 6. It can be seen that the combined induction of BCG and PTX could significantly reduce the sucrose preference rate of CD-1 mice ($p<0.01$) on day 27, and the induction effect was superior to that of the induction with BCG alone ($p<0.05$).
2) Open-field test The exploratory behaviors, depression-anxiety states, and spontaneous motor behaviors of mice were assessed by the same open-field test as in Example 1 before modeling and on day 28 after modeling.

Figure 7:
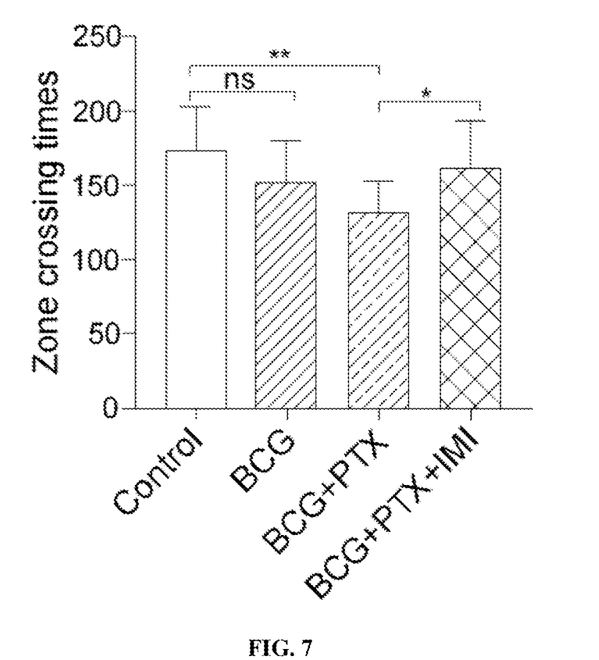
FIG. 7 shows the number of crossing of mice in each treatment group of Example 2 on day 28 in an open-field test zone (n=12, Mean±SD)
Figure 8:
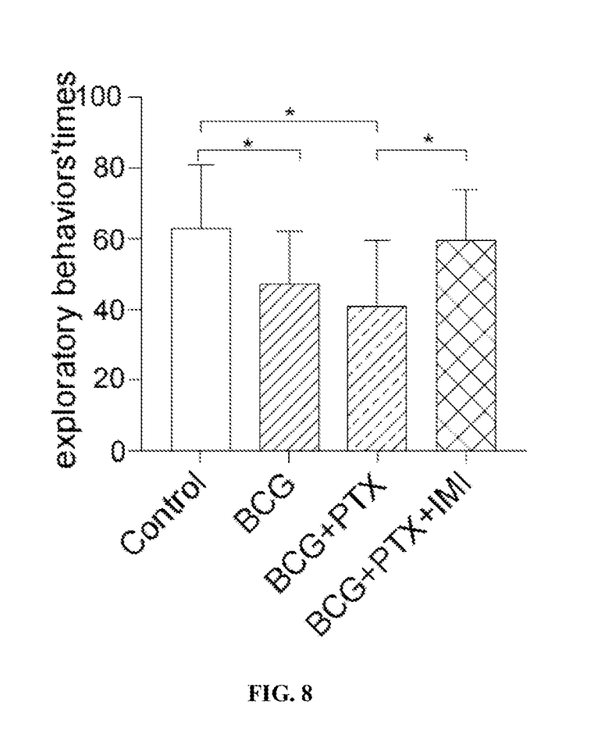
FIG. 8 shows the number of times of exploratory behaviors of mice in each treatment group of Example 2 on day 28 in an open-field test (n=12, Mean±SD)
Figure 9:
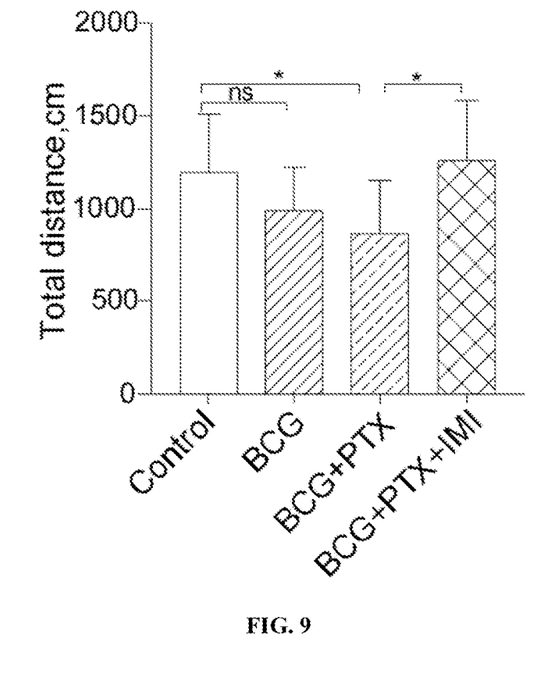
FIG. 9 shows the total movement distance of mice in each treatment group of Example 2 on day 28 (n=12, Mean±SD).

(9) Characteristics of the constructed depression mouse model
2) The mice in the BCG+PTX group were recovered from the pathological state to a normal state on day 5 (the weight loss was not significantly different from that in the Control group, $p>0.05$); the sucrose preference rate was significantly reduced on day 27 ($p<0.01$, FIG. 6); the number of times of zone crossing ($p<0.01$, FIG. 7), the exploratory behaviors ($p<0.05$, FIG. 8), and the total movement distance ($p<0.05$, FIG. 9) in the open-field test on day 28 were all decreased, indicating that the depression model induced by the combined induction of PTX and BCG exhibited prominent face validity.

3) The tricyclic antidepressant drug IMI could significantly reduce the sucrose preference rate in depression model mice ($p<0.05$, FIG. 6) at a dose of 15 mg/kg. For example, the number of times of zone crossing ($p<0.05$, FIG. 7), the exploratory behaviors ($p<0.05$, FIG. 8), and the total movement distance ($p<0.05$, FIG. 9) in the open-field test were decreased, indicating that the depression mouse model exhibited prominent predictive validity.

Example 3

(11) Preparation of PTX stock solution: a bottle of PTX (such as List Biological Labs, 50 μg/bottle, LOT #180) was taken, 250 μL of UPW was pipetted and added to the bottle, and then the bottle was shaken to obtain a clear solution as the PTX stock solution with a concentration of 200 μg/mL and stored at 4° C.

(12) Preparation of PTX working solution: PTX stock solution with a concentration of 200 μg/mL was diluted with 1×PBS to obtain the PTX working solution with a concentration of 2 μg/mL, which was prepared just before use.

(13) Preparation of BCG suspension: BCG was prepared with 1× PBS into a suspension with a CFU concentration of $5 \times 10^5$ CFU/mL.

(14) Subject animals and modeling treatment: 8-week-old SPF-grade healthy male CD-1 mice were selected and divided into a blank (Control) group and a BCG+PTX group, with 15 mice in each group.

The mice in the blank (Control) group were intraperitoneally injected (i.p.) with sterile NS at a dose of 200 μL/mouse.

The mice in the BCG+PTX group were intraperitoneally injected with 200 μL of a $5 \times 10^5$ CFU/mL BCG suspension at a CFU dose of $1 \times 10^5$ CFU/mouse on day 0, and intraperitoneally injected with 200 μL of a 2 μg/mL PTX working solution at a dose of 400 ng/mouse on day 0 and day 2. The experimental period was 15 days.

(5) Raising conditions: 5 tested CD-1 mice were raised in each cage, and single-mouse raising the mice in a single cage individually was avoided. The mice were raised in a barriered environment, and a water bottle filled with pure water and a sterile feed were placed in each cage. The mice were raised at a temperature of 23° C. and a humidity of 55%, with a 12 h light/12 h dark cycle.

(6) Monitoring of body weight changes

The body weight was measured once every day from day 4 before modeling to day 7 after modeling, and then measured once every 1 to 3 days from day 8 after modeling until the end of the experiment. The body weight changes were monitored to monitor the response of mice to pathological behaviors.

(7) Assessment of depression-like behaviors
1) Sucrose preference test

The same sucrose preference test as in Example 2 was conducted on day 14 after modeling, and the results are shown in Table 1.

2) Tail suspension test (TST)

The behavioral despair states of mice were evaluated by the same TST as in Example 1 on day 15 after modeling, and the results are shown in Table 1.

TABLE 1

| Sucrose preference test and TST results | | |
| --- | --- | --- |
| | Blank group | BCG + PTX group |
| Sucrose preference rate/% | 84.13 ± 23.60 | 67.83 ± 17.22* |
| Motionlessness time of TST/s | 77.45 ± 17.82 | 97.75 ± 24.80* |

(8) Characteristics of the constructed depression mouse model

When used in combination with PTX in mice, BCG could still successfully induce the mice in the depression model at a dose as low as $1 \times 10^5$ CFU/mouse. Mice in the BCG+PTX group were recovered from the pathological state on day 3 and then exhibited significant depression-like behaviors, for example, the sucrose preference rate on day 14 was decreased ($p < 0.05$), and the behavioral despair state in the TST on day 15 was increased ($p < 0.05$).

Example 4

The induction methods with BCG alone (high dose: $2 \times 10^7$ CFU/mouse; and low dose: $1 \times 10^6$ CFU/mouse) and a control test for the combined induction with PTX and BCG (low dose: $1 \times 10^6$ CFU/mouse) were conducted.

Preparation of PTX stock solution: a bottle of PTX (List Biological Labs, 50 μg/bottle, LOT: #181) was taken, 250 μL of UPW was pipetted and added to the bottle, and then the bottle was shaken to obtain a clear solution, as the PTX stock solution with a concentration of 200 μg/mL and stored at 4° C. for a long time.

Preparation of PTX working solution: the PTX stock solution with a concentration of 200 μg/mL was diluted with 1×PBS to obtain the PTX working solution with a concentration of 2 μg/mL, which was prepared just before use.

Preparation of high-dose BCG suspension: BCG (Chengdu Institute of Biological Products Co., Ltd.) was prepared with NS into a suspension with a CFU concentration of $1 \times 10^8$ CFU/mL.

Preparation of low-dose BCG suspension: BCG (Chengdu Institute of Biological Products Co., Ltd.) was prepared with NS into a suspension with a CFU concentration of $5 \times 10^6$ CFU/mL.

Subject animals and modeling treatment: 8-week-old SPF-grade healthy male CD-1 mice were selected and divided into a blank group, a high-dose BCG group, a low-dose BCG group, and a low-dose BCG+PTX group, with 12 mice in each group.

The mice in the blank group were intraperitoneally injected (i.p.) with sterile NS at 200 μL/mouse.

The mice in the high-dose BCG group were intraperitoneally injected with 200 μL of a $1 \times 10^8$ CFU/mL BCG suspension at a dose of $2 \times 10^7$ CFU/mouse on day 0.

The mice in the low-dose BCG group were intraperitoneally injected with 200 μL of a $5 \times 10^6$ CFU/mL BCG suspension at a dose of $1 \times 10^6$ CFU/mouse on day 0.

The mice in the low-dose BCG+PTX group were intraperitoneally injected with 200 μL of a $5 \times 10^6$ CFU/mL BCG suspension at a dose of $1 \times 10^6$ CFU/mouse on day 0, and then the mice were intraperitoneally injected with 100 μL of a 2 μg/mL PTX solution at a dose of 200 μg/mouse/time on day 1 and day 3.

(6) Raising conditions: 4 tested CD-1 mice were raised in each cage, and raising the mice in a single cage was avoided. The mice were raised in a barriered environment, and a water bottle filled with pure water and sterile feed were placed in each cage. The mice were raised at a temperature of 22° C. and a humidity of 50%, with a 12 h light/12 h dark cycle.

(7) Assessment of depression-like behaviors
1) Open-field test

The same open-field test as in Example 1 was conducted on day 28 after modeling, and the results are shown in Table 2.

2) Tail suspension test

The behavioral despair states of mice were evaluated by the same TST as in Example 1 on day 30 after modeling.

The results are shown in Table 2. By using the modeling method with the combination of PTX and BCG, the mouse depression model could be successfully constructed at a low BCG dose.

TABLE 2

| Comparison of depression-like behaviors in mice induced by low-dose BCG + PTX, high-dose BCG, and low-dose BCG | | | | | |
|---|---|---|---|---|---|
| | | Blank group | High-dose BCG group | Low-dose BCG group | Low-dose BCG + PTX group |
| Open-field test | Number of times of zone crossing | 149.70 ± 31.49 | 104.91 ± 35.1528 | 138.73 ± 23.44 | 109.2 ± 22.33 |
| | Number of times of exploratory behaviors | 46.83 ± 14.74 | 23.83 ± 12.41 | 38.92 ± 15.96 | 26.76 ± 12.41 |
| | Total movement distance/cm | 1000.18 ± 241.86 | 582.74 ± 211.42 | 734.20 ± 349.87 | 644.4 ± 107.66 |
| TST | Motionlessness time/s | 80.444 ± 15.56 | 122.60 ± 34.11 | 98.84 ± 21.35 | 119.49 ± 25.81 |

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A method for constructing a long-acting depression animal model, comprising a step of administering Bacille Calmette-Guerin (BCG) and pertussis toxin (PTX) for combined induction, comprising:

intraperitoneally injecting 50 μL to 400 μL of a working solution of BCG into a mouse on day 0, and intraperitoneally injecting 50 μL to 400 μL of a working solution of PTX into the mouse on day 0 to day 1 and day 2 to day 3;

wherein the working solution of BCG has an *M. bovis* CFU concentration of $1\times10^6$ to $6\times10^7$ CFU/mL; and the working solution of PTX has a concentration of 0.5 μg/mL to 4 μg/mL.

2. The method according to claim 1, wherein the working solution of BCG is prepared through the following step: diluting BCG with 1× phosphate buffered saline or normal saline until a colony forming unit (CFU) concentration of *Mycobacterium bovis* (*M. bovis*) is $1\times10^6$ to $6\times10^7$ CFU/mL to obtain the working solution of BCG.

3. The method according to claim 1, wherein the working solution of PTX is prepared through the following steps: dissolving PTX in ultrapure water to prepare a 200 μg/mL stock solution; and diluting the stock solution to 0.5 μg/mL to 4 μg/mL with 1× phosphate buffered saline or normal saline to obtain the working solution of PTX.

4. The method according to claim 2, wherein the model animal is a mouse.

5. The method according to daim 1, wherein than *M. bovis* CFU dose of BCG is $1\times10^5$ to $5\times10^6$ CFU/mouse; and PTX is intraperitoneally injected at a dose of 50 to 800 ng/mouse/injection.

* * * * *